July 31, 1973
A. EIKELENBOOM
Plant Pat. 3,378
CHRYSANTHEMUM PLANT
Filed Sept. 21, 1971
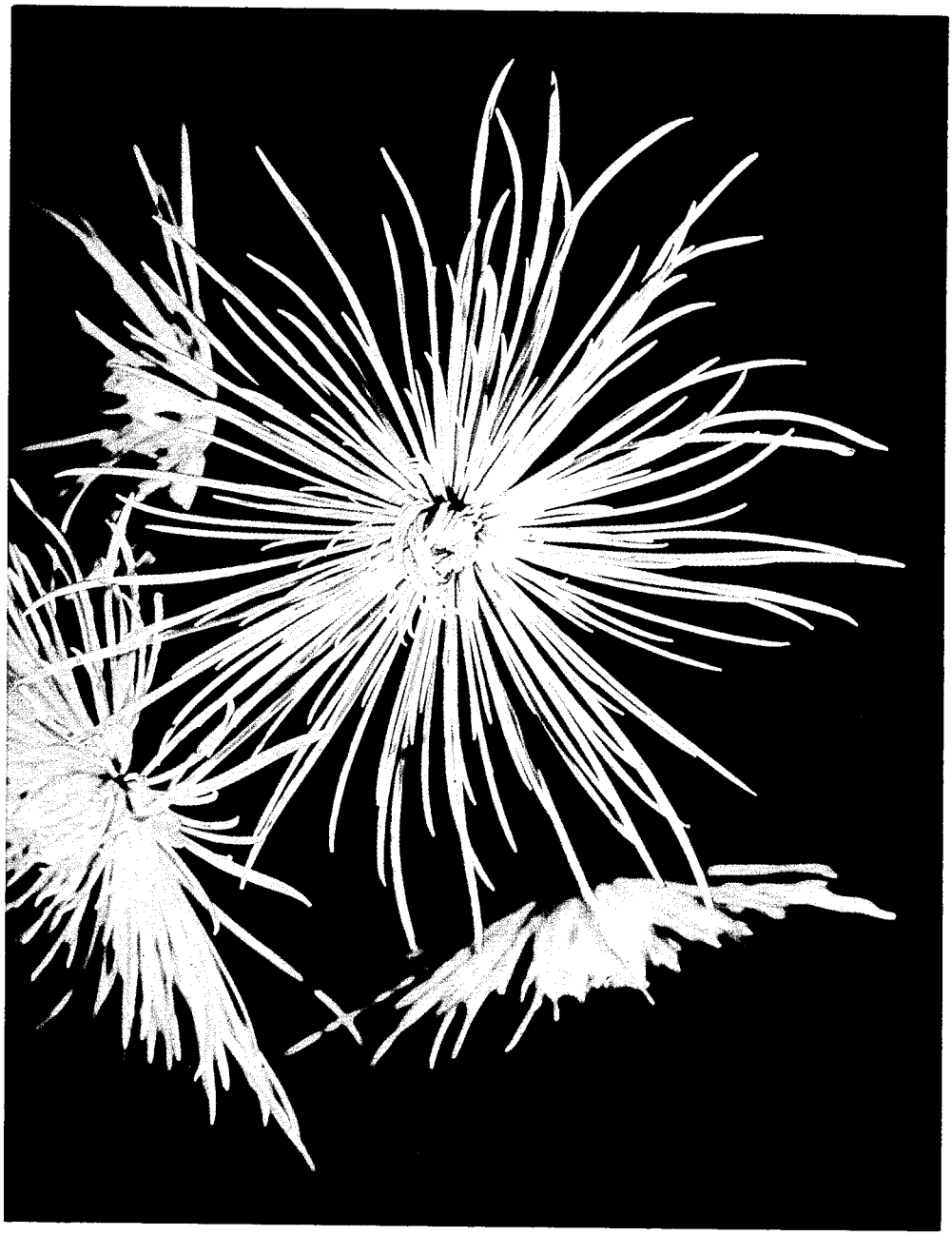

United States Patent Office

Plant Pat. 3,378
Patented July 31, 1973

3,378

CHRYSANTHEMUM PLANT

Adriaan Eikelenboom, Sotaweg 24, Oude Wetering, Netherlands

Filed Sept. 21, 1971, Ser. No. 182,566
Int. Cl. A01h 5/00
U.S. Cl. Plt.—76 1 Claim

ABSTRACT OF THE DISCLOSURE

A new and distinct variety of chrysanthemum discovered as a sport from a lot of plants of the chrysanthemum variety Tokyo, but having distinct characteristics differing materially from that variety.

SUMMARY OF THE INVENTION

This is a new and distinct variety of chrysanthemum which originated as a selected, cultivated plant, part of a lot of plants of the chrysanthemum variety Tokyo, grown by me or cultivated under my special control and supervision. This lot of plants of the chrysanthemum variety Tokyo was grown from cuttings derived from other plants of the same variety grown by me in my greenhouse.

This new variety was found in 1969 and was selected because of its new characteristics never previously exhibited in chrysanthemums or in any form, variety or selection thereof of which I am aware. Reproduction by cuttings was performed by me at Oude Wetering, Netherlands, showing that all of the improved characteristics and distinctions come true and are established and transmitted through succeeding propagations.

BRIEF DESCRIPTION OF THE DRAWINGS

The accompanying drawing shows in color one specimen of the variety in the foreground among four flowers of the same variety, as nearly true as is possible in a color illustration of this character.

DETAILED DESCRIPTION OF DISCLOSURE

In the following description, the color designations are those of the Munsell-Notation.

The novelty and distinctiveness of my new chrysanthemum variety are evident by the following outstanding characteristics, which differentiate it from the chrysanthemum variety Tokyo and differentiate it from all other varieties as well:

(1) The flower is of the "spider-type" and is composed of tube form petals without little hooks at the ends of the petals, and by this is distinctive from Tokyo. The total diameter of the flower is about 17 cm. The length of the outer petals is about 8 cm.; the diameter of the tube-forming petal is +2 mm. The petals from the outer to the inner ones to the heart of the flower are gradually shorter (about 2 cm.) and thinner (to 1 mm.). With Tokyo the change from outer longer petals to the inner smaller petals is not as gradual as with my variety. With Tokyo the first rows of petals are of almost equal length and the next following rows of petals (to the heart of the flower) are more abruptly shorter petals. Another typical characteristic of my variety is the fact that the inner petals in the heart of the flower are spirally placed in the direction as the sun turns. No other known spider type variety, especially Tokyo has this characteristic. The petals are almost straight. With Toyko, the ends of the outer petals are more or less drooping, while the inner petals, especially in the heart of the flower, are curly.

(2) The color of the petals of the variety, according to the Munsell-Notation is as follows: the outer petals are purely white or 10/0; going to the inner petals, there is a gradual change in color to yellow-greenish, about 7/5 to 8/6.

(3) The leaves are dark-green. The plant grows vigorously, more so than Tokyo, but otherwise resembles Toyko in foliage. The plant has branches beginning low on the stem which also bear flowers resulting in a terrace-like flowering plant.

(4) The stalk is firm and robust; with Tokyo the stalk is less firm.

(5) As a cut flower, the variety lasts a very long time, as do the leaves (minimum three weeks). With Toyko, the flower and leaves last half of the time of my new variety.

(6) The variety is resistant against diseases, especially against *Puccinia horriana* and is not susceptible to lice.

(7) The response period of this variety is 9 weeks; the normal blooming period at Oude Wetering, Netherlands is November 1.

The new variety of chrysanthemum is of the general type of the variety Tokyo but capable of year round culture and having generally the same characteristics of Tokyo, differing therefrom in some important ways: by a still more decorative flower, stylized in a more modern way; by a greater durability of the flower; by a plant resistant from diseases for which the Tokyo variety is more or less susceptible; and by a plant which can be multiplied more easily than Tokyo. The plant which I have discovered and selected has these several characteristics never previously exhibited in chrysanthemums to my knowledge.

I claim:

1. A new and distinct variety of chrysanthemum of improved characteristics, distinguished by its spider-type flower with tube form petals without hooks on the ends, distinctive color changing from pure white at the outer petals to yellow-greenish at the center, and by a disease resistant plant which is easily propagated, substantially as shown and described.

References Cited

California-Florida Plant Corporation, 1965, Wholesale Catalog, pp. 12, 34, 44, and 47 relied on.

ROBERT E. BAGWILL, Primary Examiner